United States Patent [19]
Rudolf et al.

[11] Patent Number: 5,179,090
[45] Date of Patent: Jan. 12, 1993

[54] CONDENSED DIAZEPINONES AND MEDICAMENTS CONTAINING THESE COMPOUNDS

[76] Inventors: Klaus Rudolf, Marktplatz 38;
Wolfhard Engel, Mozartstrasse 13;
Wolfgang Eberlein, Obere Au 6, all of D-7950 Biberach 1; Gunter Trummlitz, Buchenweg 27, D-7951 Warthausen; Gerhard Mihm, Nickeleshalde 5/1, D-7950 Biberach 1; Henri Doods, Hornsteinweg 7, D-7951 Warthausen; Norbert Mayer, Friedrich-Ebert-Strasse 66, D-7950 Biberach 1, all of Fed. Rep. of Germany

[21] Appl. No.: 779,203

[22] Filed: Oct. 18, 1991

Related U.S. Application Data

[63] Continuation of Ser. No. 580,893, Sep. 11, 1990, abandoned.

Foreign Application Priority Data

Sep. 11, 1989 [DE] Fed. Rep. of Germany ....... 3930266

[51] Int. Cl.$^5$ .................. A61K 31/55; C07D 521/00
[52] U.S. Cl. ................................ 514/220; 540/495
[58] Field of Search ..................... 540/495; 514/220

[56] References Cited

U.S. PATENT DOCUMENTS

| | | | |
|---|---|---|---|
| 4,256,747 | 3/1981 | Tauber et al. | 424/250 |
| 4,381,301 | 4/1983 | Rainer | 424/250 |
| 4,550,107 | 10/1985 | Engel et al. | 514/220 |
| 4,931,436 | 6/1990 | Engel et al. | 514/220 |
| 4,971,966 | 11/1990 | Engel et al. | 514/220 |
| 5,002,943 | 3/1991 | Mihm et al. | 514/220 |
| 5,026,694 | 6/1991 | Mihm et al. | 514/220 |

*Primary Examiner*—Robert T. Bond
*Attorney, Agent, or Firm*—D. E. Frankhouser; M. M. Timbers; A. R. Stempel

[57] ABSTRACT

Condensed diazepinones of general formula I

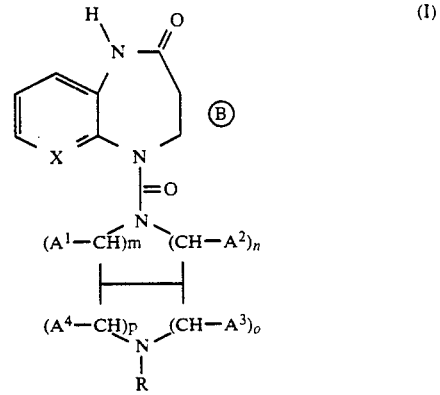

in which

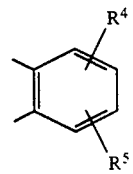 represents one of the divalent groups

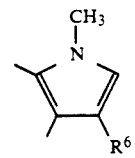 (S)

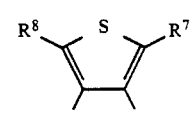

(T)

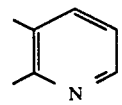

(U)

(V)

X is a =CH— group or a nitrogen atom,

R represents a lower alkyl radical, which may optionally be further substituted by a phenyl optionally carrying halogen, methyl or methoxy, $R^4$ and $R^5$ represent hydrogen, halogen or lower alkyl, $R^6$ is hydrogen, chlorine or methyl, $R^7$ and $R^8$ denote lower alkyl, $R^8$ also additionally denotes halogen, and (Abstract continued on next page.)

m, n, o and p represent the numbers 0, 1, 2 or 3 with the following limitations: the sum of m+n and the sum of o+p each denote the numbers 1, 2 or 3, the sum of n+o and the sum of m+p each denote the numbers 1, 2, 3, 4 or 5, wherein, however, the sum of m+n+o+p must always be greater than 2, and $A^1$, $A^2$, $A^3$ and $A^4$ denote hydrogen, or, for the case where m, n, o and p each denote the number 1, $A^1$ and $A^2$ together or $A^3$ and $A^4$ together represent an ethylene bridge, are suitable for the treatment of cholinergically induced spasms and motility disorders of the gastrointestinal tract and in the region of the evacuating bile ducts, for the symptomatic treatment of cystitis and of spasms from urelithiasis, for the treatment of relative incontinence, for the symptomatic treatment of bronchial asthma and bronchitis, and for the treatment of ischaemic heart diseases. The compounds are characterized by good selectivity.

11 Claims, No Drawings

CONDENSED DIAZEPINONES AND MEDICAMENTS CONTAINING THESE COMPOUNDS

This is a continuation, of application Ser. No. 580,893, filed Sep. 11, 1990, now abandoned.

The invention relates to novel condensed diazepinones, processes for their preparation and medicaments containing these compounds.

Condensed diazepinones having ulcer-inhibiting and gastric secretion-inhibiting properties are already known from EP-A-039519 and EP-A-57428 and from U.S. Pat. Nos. 3,660,380; 3,619,159; 4,213,984; 4,213,985; 4,210,648, 4,410,527; 4,424,225; 4,424,222 and 4,424,226.

EP-A-156191 (U.S. Pat. No. 4,550,107) discloses condensed diazepinones for which completely different, valuable pharmacological properties compared to the compounds of the abovementioned publications, may be induced by introducing novel aminoacyl radicals. Surprisingly, the compounds of the present application have a further active quality differing from the above effects, in spite of closer structural relationship, compared to the abovementioned ulcer-inhibiting condensed diazepinones and the previously mentioned antibradycardic condensed diazepinones. The compounds of the invention are suitable for the treatment of cholinergically induced spasms and motility disturbances in the gastrointestinal tract and in the region of the evacuating bile ducts, for the symptomatic treatment of cystitis and of spasms from urelithiasis by reducing the pathologically increased tone of hollow organs, for treatment of relative incontinence which is caused by inadequacy of sphincter and detrusor tonus, for the symptomatic treatment of bronchial asthma and bronchitis by suppressing the muscarine-induced portion of bronchoconstriction, and for the treatment of ischaemic heart diseases by reducing the heart rate and suppressing parasympathetically caused coronary spasms at the same time and reducing the basal coronary tonus. The condensed diazepinones of the invention show the effects indicated with greater selectivity, and in particular are free of tachycardiac side-effects within the therapeutically relevant dosage range.

The novel condensed diazepinones have the general formula I

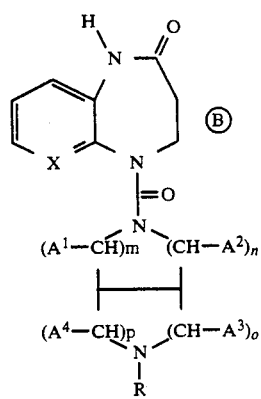

in which
Ⓑ represents one of the divalent groups

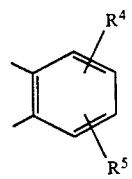   (S)

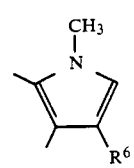   (T)

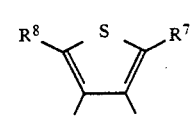   (U)

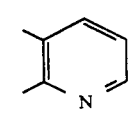   (V)

and
X, R, $R^4$, $R^5$, $R^6$, $R^7$, $R^8$, m, o, p and $A^1$, $A^2$, $A^3$ and $A^4$ have the following meanings:

X is a =CH—group or a nitrogen atom,

R is a straight-chain or branched alkyl radical having 1 to 4 carbon atoms, which may optionally also be substituted by a phenyl monosubstituted or disubstituted by chlorine, bromine, fluorine, methyl or methoxy, $R^4$ and $R^5$, which may be the same or different from one another, denote a hydrogen, fluorine, chlorine or bromine atom or an alkyl group having 1 to 4 carbon atoms, $R^6$ is a hydrogen or chlorine atom or a methyl group, $R^7$ and $R^8$, which may be the same or different from one another, denote hydrogen atoms or alkyl groups having 1 to 4 carbon atoms, however, $R^8$ may also additionally denote a halogen atom, m, n, o and p each denote the numbers 0, 1, 2 or 3 with the following limitations:

the sum of m+n and the sum of o+p each denote the numbers 1, 2 or 3, the sum of n+o and the sum of m+p each denote the numbers 1, 2, 3, 4 or 5, wherein, however, the sum of m+n+o+p must always be greater than 2, $A^1$, $A^2$, $A^3$ and $A^4$ denote hydrogen atoms; for the case where m, n, o and p each denote the number 1, either $A^1$ and $A^2$ together or $A^3$ and $A^4$ together may also represent an ethylene bridge.

To illustrate the moiety of the general formula

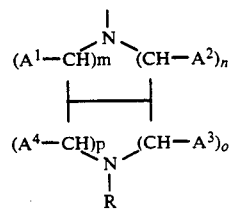

the following structures may be mentioned:

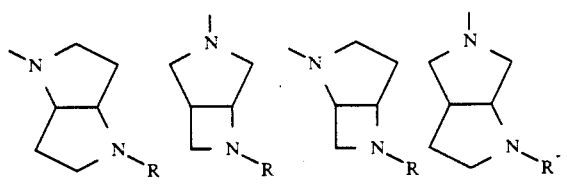
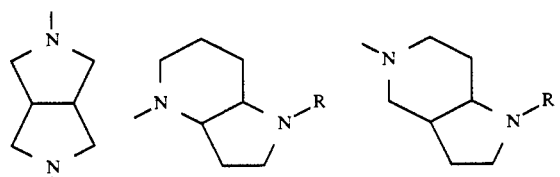
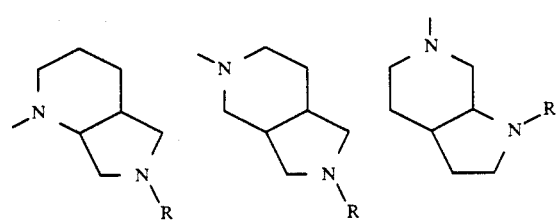
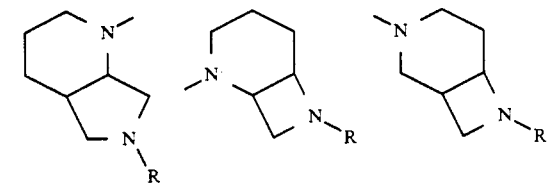
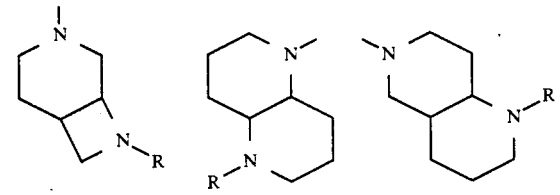
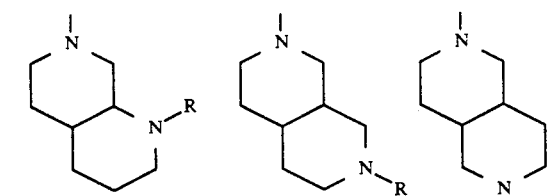
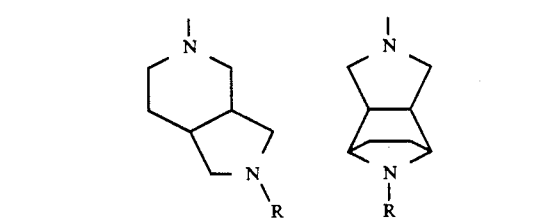

wherein in the individual ring systems the bond to the carbonyl group at the tricyclic structure of one nitrogen atom may also be exchanged for the radical R of the other nitrogen atom, the groups may also be present as cis or trans isomers as long as they fulfil the criteria mentioned hereinafter.

Preferred compounds of the above general formula I are those in which either

X denotes a nitrogen atom and ]$\textcircled{B}$ denotes the group (S) or

X denotes a =CH—group and ]$\textcircled{B}$ the group (V),

R represents a methyl group, and $R^4$ and $R^5$, which may be the same or different from one another, each represent a hydrogen, fluorine or chlorine atom, a methyl or ethyl group, and m=0, n=2, o=0, p=2 or m, n, o and p are each equal to 1.

The compounds of general formula I may also be present in the form of their physiologically acceptable salts after reaction with inorganic or organic acids. Hydrochloric acid, hydrobromic acid, sulphuric acid, methylsulphuric acid, phosphoric acid, tartaric acid, fumaric acid, citric acid, maleic acid, succinic acid, gluconic acid, malic acid, p-toluenesulphonic acid, methanesulphonic acid or amidosulphonic acid have proved to be suitable examples of acids.

To illustrate the subject of the invention, the following compounds may be mentioned as examples:

5,11-dihydro-11-[[7-methyl-3,7-diazabicyclo[3,3,0]oct-3-yl]-carbonyl]-6H-pyrido[2,3-b][1,4]benzodiazepin-6-one 9-chloro-5,11-dihydro-11-[[7-methyl-3,7-diazabicyclo[3,3,0]oct-3-yl]-carbonyl]-6H-pyrido[2,3-b][1,4]benzodiazepin-6-one 6,11-dihydro-11-[[7-methyl-3,7-diazabicyclo[3,3,0]oct-3-yl]-carbonyl]-5H-pyrido[2,3-b][1,5]benzodiazepin-5-one L-5,11-dihydro-11-[[6-methyl-2,6-diazabicyclo[3,3,0]oct-2yl]-carbonyl]-6H-pyrido[2,3-b][1,4]benzodiazepin-6-one L-5,11-dihydro-8-methyl-11-[[6-methyl-2,6-diazabicyclo [3,3,0]oct- 2-yl]-carbonyl]-6H-pyrido[2,3-b][1,4]benzodiazepin-6-one L-6,11-dihydro-11-[[6-methyl-2,6-diazabicyclo[3,3,0]oct-2-yl]-carbonyl]-5H-pyrido[2,3-b][1,5]benzodiazepin-5-one D-5,11-dihydro-11-[[6-methyl-2,6-diazabicyclo[3,3,0]oct-2-yl]-carbonyl]-6H-pyrido[2,3-b][1,4]benzodiazepin-6-one D-5,11-dihydro-8-ethyl-11-[[6-methyl-2,6-diazabicyclo[3,3,0]oct-2-yl]-carbonyl]-6H-pyrido[2,3-b][1,4]benzodiazepin-6-one D-6,11-dihydro-11-[[6-methyl-2,6-diazabicyclo[3,3,0]oct-2-yl]-carbonyl]-5H-pyrido[2,3-b][1,5]benzodiazepin-5-one L-5,11-dihydro-11-[[6-isopropyl-2,6-diazabicyclo[3.3.0]oct-2-yl]-carbonyl]-6H-pyrido[2,3-b][1,4]benzodiazepin-6-one L-5,11-dihydro-11-[[6-isobutyl-2,6-diazabicyclo[3.3.0]oct-2-yl]-carbonyl]- 6H-pyrido[2,3-b][1,4]benzodiazepin-6-one cis-5,11-dihydro-11-[[8-methyl-2,8-diazabicyclo[4.4.0]dec-2-yl]-carbonyl]-6H-pyrido[2,3-b][1,4]benzodiazepin-6-one trans-5,11-dihydro-11-[[8-methyl-2,8-diazabicyclo[4.4.0]dec-2-yl]-carbonyl]-6H-pyrido[2,3-b][1,4]benzodiazepin-6-one 5,11-dihydro-11-[[10-methyl-4,10-diazatricyclo[5.2.1.0$^{2.6}$]dec-4- yl]-carbonyl]-6H-pyrido[2,3-b][1,4]-benzodiazepin-6-one 5,11-dihydro-11-[[10-methyl-4,10-diazatricyclo[5.2.1.0²·⁶]dec-4- yl]-carbonyl]-6H-dibenzo[2,3-b][1,4]diazepin-6-one
5,11-dihydro-11-[[2-methyl-2,7-diazabicyclo[3.3.0]oct-7-yl]-carbonyl]-6H-pyrido[2,3-b][1,4]benzodiazepin-6-one
6,11-dihydro-11-[[2-methyl-2,7-diazabicyclo[3.3.0]oct-7-yl]-carbonyl]-5H-pyrido[2,3-b][1,5]benzodiazepin-5-one
5,11-dihydro-11-[[7-methyl-2,7-diazabicyclo[3.3.0]oct-2-yl]-carbonyl]-6H-pyrido[2,3-b][1,4]benzodiazepin-6-one
6,11-dihydro-11-[[7-methyl-2,7-diazabicyclo[3.3.0]oct-2-yl]-carbonyl]-5H-pyrido[2,3-b][1,5]benzodiazepin-5-one
6,11-dihydro-11-[[3-methyl-3,6-diazabicyclo[3.2.0]hept-6yl]-carbonyl]-5H-pyrido[2,3-b][1,5]benzodiazepin-5-one
5,11-dihydro-11-[[3-methyl-3,6-diazabicyclo[3.2.0]hept-6yl]-carbonyl]-6H-pyrido[2,3-b][1,4]benzodiazepin-6-one
5,11-dihydro-11-[[6-methyl-3,6-diazabicyclo[3.2.0]hept-3-yl]-carbonyl]- 6H-pyrido[2,3-b][1,4]benzodiazepin-6-one
6,11-dihydro-11-[[6-methyl-3,6-diazabicyclo[3.2.0]hept-3yl]-carbonyl]-5H-pyrido[2,3-b][1,5]benzodiazepin-5-one
5,11-dihydro-11-[[3-methyl-3,8-diazabicyclo[4.2.0]oct-8-yl]-carbonyl]-6H-pyrido[2,3-b][1,4]benzodiazepin-6-one
trans-5,11-dihydro-11-[[7-methyl-2,7-diazabicyclo[4.4.0]dec-2-yl]-carbonyl]-6H-pyrido[2,3-b][1,4]benzodiazepin-6-one
trans-6,11-dihydro-11-[[7-methyl-2,7-diazabicyclo[4.4.0]dec-2-yl]-carbonyl]-5H-pyrido[2,3-b][1,5]benzodiazepin-5-one
5,11-dihydro-11-[[8-methyl-3,8-diazabicyclo[4.2.0]oct-3-yl]-carbonyl]-6H-pyrido[2,3-b][1,4]benzodiazepin-6-one
5,11-dihydro-11-[[3-methyl-3,7-diazabicyclo[4.2.0]oct-7-yl]-carbonyl]-6H-pyrido[2,3-b][1,4]benzodiazepin-6-one
5,11-dihydro-11-[[7-methyl-3,7-diazabicyclo[4.2.0]oct-3-yl]-carbonyl]-6H-pyrido[2,3-b][1,4]benzodiazepin-6-one
5,11-dihydro-11-[[3-methyl-3,8-diazabicyclo[4.3.0]non-8-yl]-carbonyl]-6H-pyrido[2,3-b][1,4]benzodiazepin-6-one
5,11-dihydro-11-[[8-methyl-3,8-diazabicyclo[4.3.0]non-3-yl]-carbonyl]-6H-pyrido[2,3-b][1,4]benzodiazepin-6-one
L-4,9-dihydro-3-methyl-4-[[6-methyl-2,6-diazabicyclo[3.3.0]oct-2-yl]-carbonyl]-10H-thieno[3,4-b][1,5]benzodiazepin-10-one
4,9-dihydro-3-methyl-4-[[7-methyl-3,7-diazabicyclo[3.3.0] oct-3-yl]-carbonyl]-10H-thieno[3,4-b][1,5]benzodiazepin-10-one
L-3-chloro-1-methyl-4-[[6-methyl-2,6-diazabicyclo[3.3.-0]oct-2-yl]-carbonyl]-1,4,9,10-tetrahydropyrrolo[3,2-b][1,5]benzodiazepin-10-one
3-chloro-1-methyl-4-[[7-methyl-3,7-diazabicyclo[3.3.-0]oct-3-yl[-carbonyl]-4,9,10-tetrahydropyrrolo[3,2-b][1,5]benzodiazepin-10-one The novel basic substituted condensed diazepinones of the general formula I are obtained in accordance with the invention by the following processes:

a) basic substituted condensed diazepinones of general formula Ia

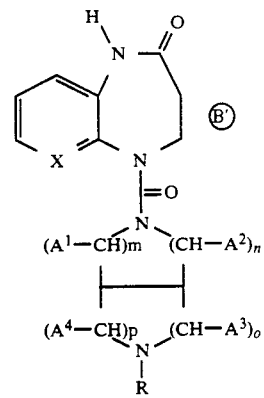

in which X, R, R⁴, R⁵, R⁶, R⁷, R⁸, m, n, o, p, A¹, A², A³ and A⁴ have the meanings indicated above and ]ⒷⒷ represents one of the divalent radicals (S), (U), (V) or (T')

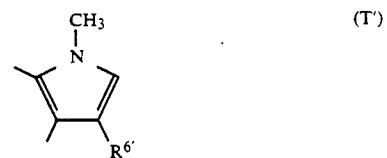

wherein R⁴' is a chlorine atom or a methyl group, are obtained by reacting carbonic acid derivatives of general formula II

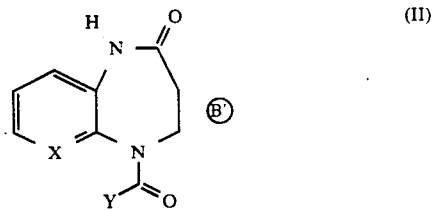

in which ]ⒷⒷ and X have the meanings indicated and Y denotes a halogen atom, preferably a bromine or chlorine atom, or denotes the group OR¹¹, wherein R¹¹ represents an optionally halogen-substituted alkyl group having 1 to 5 carbon atoms, a phenyl group optionally substituted by halogen atoms or nitro groups, or an aralkyl group having 7 to 15 carbon atoms, with compounds of the general formula III,

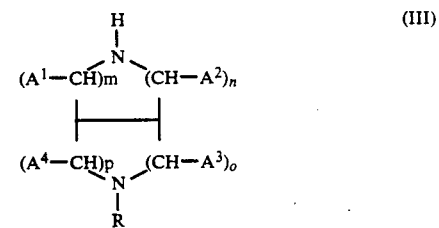

in which
R, m, n, o, p,
A¹, A², A³ and A⁴ are defined as above.

The reaction is carried out without or preferably in the presence of solvents, such as for example water, toluene, or alcohols, such as for example methanol, ethanol or isopropanol, but most preferably in the presence of aprotic polar solvents, for example tetrahydrofuran, 1,4-dioxane, acetonitrile, N,N-dimethylformamide, dimethylsulphoxide, hexamethylphosphoric acid triamide, or mixtures thereof, and at temperatures between $-10°$ C. and the boiling point of the reaction mixture, preferably between 40° and 100° C. The use of additional inorganic or organic bases, for example alkali metal or alkaline earth metal hydroxides, alcoholates or carbonates, for example sodium hydroxide, sodium methoxide, potassium tert.butoxide, sodium carbonate, potassium carbonate; tertiary amines, for example triethylamine, ethyldiisopropylamine, N,N-dimethylaniline, pyridine or 4-(dimethylamino)pyridine; and reaction in the presence of an excess of a compound of general formula III, have proved to be advantageous.

If the bicyclic diamines of general formula III and the carbonic acid derivatives of general formula II are used in equimolar amounts, if Y denotes a halogen atom the hydrohalic acid salts of the required compounds of general formula Ia are obtained directly.

However, the reaction may also be carried out using a metal compound of general formula IIIa,

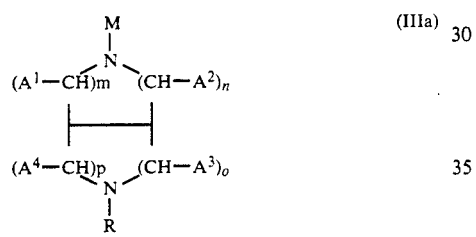

in which

M denotes an alkali metal atom or 1 equivalent of an alkaline earth metal atom. Thus metal compounds of the general formula IIIa can be easily prepared in situ from III by reacting with alkali metals or alkaline earth metals, for example with sodium, potassium or barium, or with alkali metal or alkaline earth metal hydrides, for example with sodium, potassium or calcium hydride, or by reaction with alkali metal or alkaline earth metal organometallic compounds for example with n-butyl lithium or phenyl lithium.

b.) basic substituted condensed diazepinones of general formula Ia can also be obtained by reacting tricyclic of general formula IV

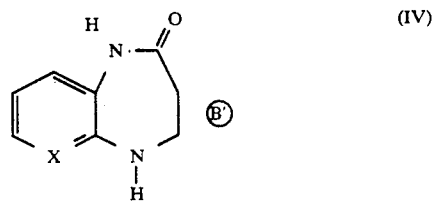

in which X and

]$\textcircled{B}$ are defined as above, with a chlorocarbonic acid derivative of general formula V

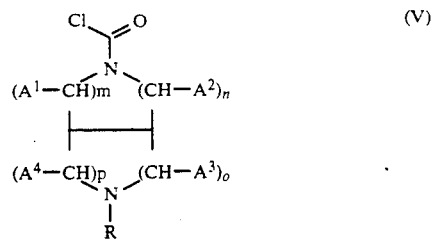

wherein R, m, n, o, p, $A^1$, $A^2$, $A^3$ and $A^4$ have the abovementioned meanings.

The reaction is preferably carried out in inert organic solvents, for example in aromatic hydrocarbons, such as toluene, xylene, in ethers such as diisopropylether, tetrahydrofuran or dioxane, in ketones such as 3-pentanone, in chlorinated aliphatic hydrocarbons such as 1,2-dichloroethane, or in other solvents, such as acetonitrile or dimethylformamide, or in mixtures thereof, optionally in the presence of tertiary organic bases, such as pyridine, and at temperatures up to the boiling point of the reaction mixture, preferably at temperatures between $+30$ and $+100°$ C.

c) the novel pyrrolo-condensed diazepinones of general formula Ib covered by general formula I

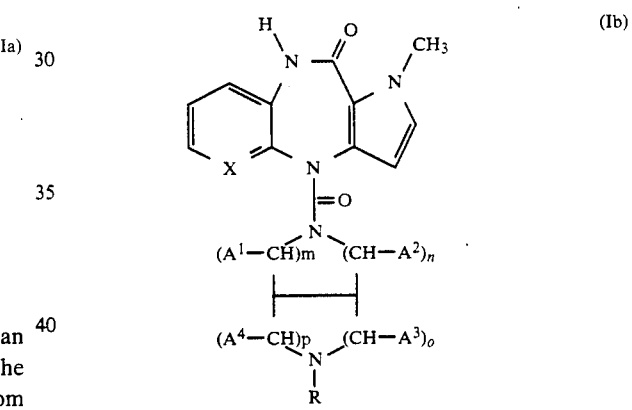

wherein X, R, m, n, o, p, $A^1$, $A^2$, $A^3$ and $A^4$ have the meanings mentioned in the introduction, may also be prepared by the hydrogenolysis of compounds of general formula Ia, in which $R^{6'}$ denotes a chlorine atom.

The hydrogenolysis is carried out in the presence of catalysts based on metals from the VIIIth sub-group of the periodic table of elements, for example palladium on animal charcoal, palladium on barium sulphate, Raney nickel or Raney cobalt, and at hydrogen pressures of 1 to 300 bar and temperatures of 0° C. to 130° C. in the presence of solvents, for example alcohols, such as methanol, ethanol; ethers, such as dioxane, tetrahydrofuran; carboxylic acids, for example acetic acid; or tertiary amines, for example triethylamine. If the process is thus carried out in the absence of additional hydrogen chloride acceptors, for example sodium carbonate, potassium hydrogen carbonate, triethylamine or sodium acetate, the hydrochlorides of the required compounds, which may be obtained by evaporating tne reaction solution after removing the catalyst, are produced directly. If the hydrogen in the above hydrogenolysis reaction is replaced by formic acid, the reaction proceeds in principle even without pressure. The reaction with formic acid in the presence of dimethylformamide as solvent and palladium on charcoal as catalyst at temperatures between 70° and 110° C., and reduction using triethylammonium formate in the presence of excess triethylamine and palladium on animal charcoal or palladium acetate and triarylphosphines, such as triphenylphosphine, tris-(o-tolyl)phosphine, tris-(2,5-diisopropylphenyl)phosphine, at temperatures between 40° and 110° C., have proved to be particularly advantageous for these variants.

Bases of the general formula I thus obtained may then be converted to their acid addition salts or the acid addition salts obtained may be converted into the free bases or other pharmacologically acceptable acid addition salts.

If m, n, o or p each have the value 1 in the aminocarbonylated condensed diazepinones of general formula I of the invention, these compounds are achiral; however, in all other cases the compounds are chiral. These chiral compounds may therefore occur in each case as (+) and (−) enantiomers. The invention includes the individual isomers as well as their racemates.

The separation of possible racemates of the compounds of general formula I may be carried out by known processes, for example using an optically active acid, such as (+) or (−) tartaric acid, or a derivative thereof, such as (+) or (−) diacetyltartaric acid, (+) or (−) monomethyltartrate or (+) camphorsulphonic acid.

For isomer separation, the racemate of a compound of general formula I is reacted with one of the optically active acids given above in a solvent in equimolar amount in accordance with a conventional process, and the crystalline diastereomeric salts obtained are separated by utilising their differing solubility. This reaction may be carried out in any type of solvent, as long as it has a sufficient difference in the solubility of the salts. Methanol, ethanol or mixtures thereof, for example in volume ratio 50:50, are preferably used. Each of the diastereomeric salts is then dissolved in water, neutralised using a base, such as sodium hydroxide or potassium hydroxide, and thus the corresponding free compound is obtained in the (+) or (−) form.

In each case only one enantiomer is obtained if the syntheses described above are carried out using only one enantiomer of general formula III or V.

The preparation of the carbonic acid derivatives of general formula II required as intermediates is described in detail in DE-Al-37 26 908.

Intermediate compounds of general formula III, some of which are novel and have not yet been previously disclosed, can be obtained, for example by the following methods:

a.) the 2-substituted 2,6-diazabicyclo[3.3 0]octanes covered by general formula III are obtained in corresponding manner or completely analogously to the instructions of Cope, A. C. and Shen, T. Y. in J. Am. Chem. Soc. 78: 5916 (1956).

The 2-benzyl-2,6-diazabicyclo[3.3.0]octane previously disclosed in this literature reference is then reacted with ethyl chloroformate to give the corresponding urethane, which is then reduced using lithium aluminium hydride to give 2-benzyl-6- methyl-2,6-diazabicyclo[3.3.0]octane. The hydrogenolytic removal of the benzyl radical produces the desired 2-methyl-2,6-diazabicyclo[3.3.0]octane.

b.) the 3-substituted 3,7-diazabicyclo[3.3.0]octanes covered by general formula III can be prepared, for example starting from pyrrole-3,4-dicarboxylic acid completely analogously to the instructions of Loftus, P. and Wong, J. J. in J. Heterocyclic. Chem. 20; 321 (1983).

Alternatively, the desired 3-substituted 3,7-diazabicyclo[3.3.0]octanes may be prepared starting from N-alkylated glycine derivatives, paraformaldehyde and maleic acid imide and then reducing the bicyclic imide produced in this [3+2] cycloaddition using lithium aluminium hydride.

c.) the 2-substituted 2,7-diazabicyclo[3.3.0]octanes covered by general formula III can be obtained in accordance with the instructions of Birkhofer L. and Feldmann H. in Annalen 677: 154 (1964).

d.) the 10-methyl-4,10-diazatricyclo[$5.2.1.0^{2,6}$]decane covered by general formula III can be obtained, for example di-methyl-N-ethoxycarbonyl-7-azabicyclo[2.2.1]2,5-dien-2,3-(dicarboxylate which is known in the literature (Bansal, R. C. et al., Can. J. Chem. 47; 2391-4 (1969). Alkaline saponification of both methyl ester groups followed by palladium-catalysed hydrogenation produces a very good yield of N-ethoxycarbonyl-7-azabicyclo[2.2.1]heptane-2,3-dicarboxylic acid. The dicarboxylic acid is cyclised with the aid of dicyclohexylcarbodiimide to the anhydride which is then heated under reflux with excess benzylamine. The 4-benzyl-10-ethoxycarbonyl-4,10-diazatricyclo[$5.2.1.0^{2,6}$]-decane-3,5-dione thus obtained in good yield is reduced using lithium aluminium hydride and the benzyl protective group is then split off by means of catalytically activated hydrogen.

e.) the 8-substituted 2,8-diazabicyclo[4.4.0]decanes covered by general formula III may be obtained, for example starting from N-substituted 4-piperidones. The enamine obtained by reaction with, for example, pyrrolidine, is initially added to acrylonitrile and the addition product is cyclised in sulphuric acid to give 8-substituted $\Delta^{1,6}$-2,8- diazabicyclo[4.4.0]decen-3-ones. Hydrogenation of the double bond using catalytically activated hydrogen preferably produces cis- linked ring systems, however, hydrogenation using triethylsilane preferably produces trans-linked ring systems. Reduction of the 8-substituted 2,8-diazabicyclo[4.4.0]decan-3-ones thus obtained to give the required 8-substituted 2,8-diazabicyclo[4.4.0]decanes proceeds smoothly using lithium aluminium hydride.

f.) the trans-7-methyl-2,7-diazabicyclo[4.4.0]decane covered by general formula III may be prepared, for example starting from 1,5-naphthyridine. Reaction with sodium in amyl alcohol produces the trans-2,7-diazabicyclo[4.4.0]-decane which is reacted with methyl chloroformate to give the monourethane (Arch. Immunol. Ther. Exp. 19; 261 (1971)). Treatment with lithium aluminium hydride produces the desired trans-7-methyl-2,7-diazabicyclo[4.4.0]decane. Alternatively, the trans-2,7-diazabicyclo[4.4.0]decane may be converted directly to the trans-7-methyl-2,7-diazabicyclo[4.4.0]decane using formaldehyde and hydrogen with addition of a catalyst.

The invention also relates to medicaments which contain one or more basic substituted diazepinones of general formula I or physiologically acceptable salts thereof.

The compounds of general formula I can be incorporated for this purpose into conventional pharmaceutical formulations, for example in solutions, suppositories, tablets, coated tablets, capsules or tea preparations (tisanes), in a manner known per se. The daily dosage is generally between 0.01 and 10 mg/kg, preferably 0.02 and 5 mg/kg, in particular 0.05 and 2.5 mg/kg of body weight, for oral administration, which daily dosage is optionally administered in the form of several, preferably 1 to 3, individual doses, to achieve the required results.

The basic substituted condensed diazepinones of general formula I and their acid addition salts have valuable properties; as already mentioned in the introduction, they show selective spasmolytic properties on peripheral organs, in particluar ileum and bladder, and are suitable in human and veterinary medicine for the treatment of cholinergically induced spasms and motility disorders in the gastrointestinal tract and in the region of the evacuating bile ducts, for the symptomatic treatment of cystitis and of spasms from urelithiasis by reducing the pathologically increased tone of the hollow organs, for the treatment of relative incontinence which is caused by inadequacy of sphincter and detrusor tonus, for the symptomatic treatment of bronchial asthma and bronchitis by suppressing the muscarine-induced portion of bronchoconstriction, and for the treatment of ischaemic heart diseases by reducing the heart rate and suppressing parasympathetically caused coronary spasms at the same time and reducing the basal coronary tonus, in spite of a lack of heart rate-increasing, gastric acid secretion-inhibiting, salivation-inhibiting effects and effects impairing the accomodation ability of the eye in the therapeutic dosage range.

A favourable relationship between spasmolytic effects on the one hand, and the undesirable effects occurring with therapeutic agents having anticholinergic active components on the heart rate, pupil width, tear, saliva and gastric acid secretion on the other hand, is particularly important for the therapeutic use of the substances. The following tests show that the compounds of the invention have surprisingly favourable relationships with regard to this.

A. Investigation of functional selectivity of the anti-muscarine effect

Substances having anti-muscarine properties inhibit the effects of exogenically introduced agonists or of acetylcholine which is released from cholinergic nerve endings. A description of methods which are suitable for determining spasmolytically active anti-muscarine agents is given below.

"In vitro" organ Preparations

Dissociation constants ($K_B$ values) were determined "in vitro" on the ileum and spontaneously beating vestibule of a guinea pig. The ileum was removed and incubated in an organ bath in Krebs- Henseleit solution. Contractions were induced by increasing concentrations of methacholine (M) such that complete concentration-activity graphs could be plotted. M was then washed out, the substance to be investigated was added and incubated for 30 minutes, and once again a concentration-activity graph was plotted using M.

The dissociation constant according to Arunlakshana and Schild (Brit. J. Pharmacol. 14; 48 (1959)) Was calculated from the dosage ratio (DR) which is the measure of the displacement of the concentration-activity graph.

M reduced the heart rate as a function of concentration in the removed, spontaneously beating right vestibule. This effect was cancelled again by adding an anti-muscarine agent. Dissociation constants for the muscarine receptors of the vestibule were obtained in the same manner as described above. The comparison of the dissociation constants determined in both tissues permitted the identification of selectively spasmolytically active substances. The results are contained in Table III.

"In vivo" methods

The methods used had the aim of confirming the selectivity of the anti-muscarine effect. Any substances which had been selected on the basis of "in vitro" investigations were investigated for
1. selectivity of the bronchospasmolytic activity in the guinea pig,
2. saliva secretion-inhibiting effect in the rat, and
3. in situ spasmolytic activity in the guinea pig.

1. Effect on M receptors of the bronchial tubes, the heart and the bladder of anaesthetised guinea pigs

Methods

Guinea pigs of both sexes (550–600 g body weight) were anaesthetised using urethane (1.4 g/kg intraperitoneally). A cannula was introduced into the augular vein to inject the active agents. 220 I.U./kg of heparin were injected intravenously. A cannula was introduced into the trachea; the animals were artificially respirated by means of a positive pressure pump (Braun-Melsungen) using oxygen-enriched air at a rate of 80 beats per minute. A branch of the tracheal cannula was connected to a water manometer 10 cm high. The respiration volume was set such that the maximum intratracheal pressure just reached the pressure of a 10 cm water column during respiration.

Apart from a few modifications, the effect of the active agents on the bronchial tone was measured in accordance with the method described by Konzett and Rössler (1940). The volume of respiration gas mixture (overflow), produced by bronchoconstriction, which flowed through the water manometer was measured by means of a tube pneumotachometer (FLEISCH, Model 1000), which was connected to an SP 2040D differential pressure transducer (HSE). The values were recorded using an IFD recording apparatus. The trachea was clamped for a short time before the test to produce the maximum possible degree of bronchoconstriction for calibration. A cannula was introduced into the left large carotid artery; the arterial blood pressure was measured with the aid of a pressure transducer (Bell and Howell, 4-327 I) in conjunction with an IFD recording apparatus. The heart rate was measured using a rate detector which is triggered by arterial pulse waves.

A small median abdominal incision was made and the bladder was connected to a power transducer under a resting tension of 1 gram.

The active substances to be tested were injected via the jugular vein, 5 minutes later the increase in tone of the bladder (in grams) the bronchial resistance (in %) and the decrease in heart rate (beats per minute) were measured after administration of acetylcholine (50 $\mu$g/kg intravenously and intraarterially). Dosage-dependency graphs were drawn by plotting the percentage inhibition of bronchoconstriction, bradycardia and the increase in tone of the bladder against the logarithm of the dosage (mole/kg) of the active agents to be investigated. The results are given as average values (n=4–6). Results see Table I.

2. Saliva secretion-inhibiting effect in the rat

Male THOM rats anaesthetised using 1.2 g/kg of urethane received increasing dosages of the substance intravenously in accordance with Lavy and Mulder (Arch. int. Pharmacodyn. 178; 437–445, (1969)). The secretion of saliva was triggered by subcutaneous administration of 2 mg/kg of pilocarpine. The saliva was absorbed using blotting paper, the surface taken up by it was determined planimetrically every 5 minutes. The dosage of the substance which reduced the volume of saliva by 50% was determined graphically.

For results see Table II.

3 In situ spasmolytic effect in guinea pigs

Male guinea pigs (500 to 600 g body weight) were anaesthetised using urethane (1.2 g/kg intraperitoneally); cannulae Were introduced into the trachea, jugular vein and the left carotid artery. The animals were artificially respirated by means of a positive pressure pump using oxygen-enriched air at a beat frequency of 80 per minute. A 3 to 4 cm abdominal incision was made and about 15 cm of a movable loop of the ileum was removed distally while maintaining the blood circulation. The proximal part was filled with a Krebs-Ringer solution and a pressure meter was introduced into the intestine using a Millar micro-tip catheter (PC-450, 5F). A glass tube was placed vertically in the abdomen and attached to the surrounding abdominal wall such that the animal served as its own organ bath when the glass tube was filled with Krebs-Ringer solution.

The glass tube was filled with Krebs-Ringer solution until the whole of the hypogastrium was immersed. The active agents to be tested were injected via the jugular vein; 5 minutes later contractions were produced by means of methacholine (20 μg/kg intraarterially). Dosage-activity graphs were obtained by plotting the percentage suppression of contractions produced by methacholine against the logarithm of dosage amount (mole/kg) of the active substance to be tested.

The results were given as average values (n=4 to 8) (see Table II).

The following compounds were investigated by way of example in accordance with the instructions above:

A = L-5,11-dihydro-11-[[6-methyl-2,6-diazabicyclo[3.3.0]-oct-2-yl]carbonyl]-6H-pyrido[2,3-b][1,4]benzodiazepin-6-one B = D-6,11-dihydro-11-[[6-methyl-2,6-diazabicyclo[3.3.0]-oct-2-yl]carbonyl]-5H-pyrido[2,3-b][1,5]benzodiazepin-5-one C = 5,11-dihydro-11-[[7-methyl-3,7-diazabicyclo[3.3.0]-oct-3-yl]carbonyl]-6H-pyrido[2,3-b][1,4]benzodiazepin-6-one D = 4,9-dihydro-3-methyl-4-[[7-methyl-3,7-diazabicyclo[3.3.0]-oct-3-yl]carbonyl]-10H-thieno[3,4-b][1,5]benzodiaze pin-10-one and as comparison substances X = 11-[[2-[(dimethylamino)methyl]-1-piperidinyl]acetyl]-5,11-dihydro-6H-pyrido[2,3-b][1,4]benzodiazepin-6-one (see U.S. Pat. No. 4,550,107)

Y = 5,11-dihydro-11-[(4-methyl-1-piperazinyl)acetyl]-6H-pyrido[2,3-b][1,4]benzodiazepin-6-one (Pirenzepine, see U.S. Pat. No. 3,660,380) and Z = atropine.

TABLE I

Selectivity of the bronchospasmolytic activity in the guinea pig: Acetylcholine - antagonism

| Substance | Bronchial tubes $-\log ED_{50}$ (mole × kg$^{-1}$) i.v. | Bladder $-\log ED_{50}$ (mole × kg$^{-1}$) i.v. | Heart $-\log ED_{50}$ (mole × kg$^{-1}$) i.v. | Ratio influence of Bradycardia to broncho-constriction |
|---|---|---|---|---|
| A | 7.31 | 6.31 | 5.98 | 21 |
| B | 7.35 | 6.09 | 5.71 | 44 |
| C | 6.20 | 5.52 | 5.32 | 8 |
| D | 7.05 | 5.80 | 6.13 | 8 |
| X | 5.58 | 4.93 | 5.84 | 0.5 |
| Y | 6.57 | 5.84 | 5.90 | 5 |
| Z | 8.09 | 7.28 | 7.57 | 3 |

TABLE II

Selectivity of the in situ spasmolytic activity in relation to the saliva secretion-inhibiting effect.

| Substance | In situ spasmolysis guinea pig ileum $-\log ED_{50}$ (mole × kg$^{-1}$) i.v. | Saliva secretion inhibition rat $-\log ED_{50}$ (mole × kg$^{-1}$) i.v. | Ratio saliva secretion inhibition to spasmolytic activity |
|---|---|---|---|
| A | 6.93 | 6.70 | 2 |
| C | 6.15 | 5.53 | 4 |
| Y | 6.08 | 6.42 | 0.5 |
| Z | 7.28 | 7.60 | 0.5 |

TABLE III

Dissociation constants ($K_B$ values) in the ileum and spontaneously beating vestibule of the guinea pig:

| Substance | $K_B$ [mole/liter] Heart | $K_B$ [mole/liter] Ileum | Selectivity $K_B$ heart to $K_B$ ileum |
|---|---|---|---|
| A | 2.09 × 10$^{-7}$ | 3.02 × 10$^{-8}$ | 6.9 |
| B | 1.45 × 10$^{-7}$ | 6.03 × 10$^{-8}$ | 2.4 |
| X | 1.05 × 10$^{-7}$ | 6.17 × 10$^{-7}$ | 0.17 |
| Y | 1.23 × 10$^{-7}$ | 1.94 × 10$^{-7}$ | 0.63 |
| Z | 1.41 × 10$^{-9}$ | 8.13 × 10$^{-10}$ | 1.7 |

Discussion of the results

The substances of general formula I inhibit the effects of exogenically introduced acetylcholine or methacholine on the smooth muscle of bronchial tubes, bladder or small intestine in low dosages, without the agonistic effect on the heart rate being influenced (Tables I and III). For example, the substances A and B show a very marked smooth muscle selectivity; 21 to 44 times lower dosages are necessary to inhibit the bronchoconstriction triggered by acetylcholine compared to acetylcholine-induced bradycardia (Table I). The substances of general formula I not only show selectivity for the smooth muscle compared to effects which are triggered by cardiac muscarine receptors, but higher dosages are also required to inhibit the pilocarpine- induced saliva secretion (Table II).

The observed in vivo selectivity of the substances for the smooth muscle agrees with the in vitro investigations. The substances have a higher affinity to muscarine receptors in the ileum compared to cardiac muscarine receptors (Table III).

The data show that the substances of general formula I inhibit the effects of muscarine agonists on the smooth muscle, for example bronchial tubes, bladder and ileum, in dosages which do not have any influence on the heart rate or saliva secretion. The comparison substances Y (pirenzepine) and Z (atropine) show no selectivity and influence the abovementioned effects in the same dosage range. The comparison substance X shows a higher effectiveness on cardiac muscarine receptors.

All substances of general formula I are characterised by a pronounced stabilty to hydrolysis. It is thus possible to prepare storage-stable solutions for parenteral administration.

The following examples should explain the invention in more detail: "M.p." denotes "meltinq point", "D." denotes "Decomposition".

Satisfactory elemental analyses, IR, UV, $^1$H-NMR spectra, often mass spectra as well, exist for all compounds. Percentages are always percentages by weight, unless otherwise expressly mentioned.

EXAMPLE 1

5,11-Dihydro-11-[[7-methyl-3,7-diazabicyclo[3.3.0]-oct-3-yl]carbonyl]-6H-pyrido[2,3-b][1,4]benzodiazepin-6-one A mixture of 4.9 g (18 mmoles) of 11-(chlorocarbonyl)-5,11-dihydro-6H-pyrido[2,3-b][1,4]benzodiazepin-6-one and 2.3 g of 3- methyl-3,7-diazabicyclo[3.3.-0]octane in 75 ml of dry dimethylformamide was stirred for 20 hours at ambient temperature. The reaction mixture was concentrated in vacuo, the residue was divided between 1N hydrochloric acid and methylene chloride. The organic phase was washed two further times using 1N hydrochloric acid and once using water. The combined aqueous phases were rendered basic using potassium carbonate and extracted using methylene chloride (3×150 ml). The combined methylene chloride phases were dried over magnesium sulphate, concentrated and the crude material was recrystallised from acetonitrile. 2.9 g (41% of theory) of colourless crystals of m.p. 157°–159° C. were obtained.

$C_{20}H_{21}N_5O_2$ (363.43): Calculated: C, 66.10., H, 5.82; N, 19.27, Found: 65.75, H, 5.68; N, 19.17.

EXAMPLE 2

9-Chloro-5,11-dihydro-11-[[7-methyl-3,7 TM diazabicyclo[3.3.0]oct-3-yl]carbonyl]-6H-pyrido[2,3-b][1,4]benzodiazepin-6-one Prepared analogously to Example 1 from 9-chloro-11-(chlorocarbonyl)-5,11-dihydro-6H-pyrido[2,3-b][1,4]benzodia zepin-6-one and 3-methyl-3,7-diazabicyclo[3.3.0]octane in a yield of 67% of theory. Colourless crystals of m.p. 216°–217° C. (acetonitrile).

$C_{20}H_{20}ClN_5O_2$ (397.87 Calculated: C, 60.38, H; 5.07, N, 17.50, Cl; 8.91. Found: C, 59.73, H, 5.02; N; 17.28.

EXAMPLE 3

6,11-Dihydro-11-[[7-methyl-3,7-diazabicyclo[3.3.0]oct-3-yl]carbonyl]-5H-pyrido[2.,3-b][1,5]benzodiazepin-5-one Prepared analogously to Example 1 from 11-(chlorocarbonyl)-6,11-dihydro-5H-pyrido[2,3-b][1,5]benzo diazepin-5-one and 3-methyl- 3,7-diazabicyoclo[3.3.0]octane in a yield of 7% of theory. Colourless crystals of m.p. 115°–120° C. (ethyl acetate/diisopropyl ether).

EXAMPLE 4

4,9-Dihydro-3-methyl-4-[[7-methyl-3,7-diazabicyclo[3.3.0]oct-3-yl]carbonyl]-10H-thieno[3,4-b][1,5]benzodiazepin-10-one Prepared analogously to Example 1 from 4-(chlorocarbonyl)-4,9-dihydro-3-methyl-10H-thieno[3,4-b][1,5]benzodiazepin-10-one and 3-methyl-3,7-diazabicyclo-[3.3.0]octane in a yield of 13% of theory. Colourless crystals of m.p. 220°–222° C. (ethanol).

EXAMPLE 5

3-Chloro-1-methyl-4-[[7-methyl-3,7-diazabicyclo[3.3.-0]oct-3yl]carbonyl]-1.4.9.10-tetrahydropyrrolo[3,2-b][1,5]benzodiazepin-10-one Prepared analogously to Example 1 from 3-chloro-4-(chlorocarbonyl)-4,9-dihydro-1-methyl-1.4.9.10-tetrahydropyrrolo[3,2-b][1,5]benzodiazepin-10-one and 3-methyl-3,7-diazabicyclo[3.3.0]octane in a yield of 24% of theory. Colourless crystals of m.p. >280° C. (ethanol/water).

EXAMPLE 6

L-5,11-Dihydro-11-[[6-methyl-2,6-diazabicyclo[3.3.-0]oct-2-yl]carbonyl]-6H-pyrido[2,3-b][1,4]benzodiazepin-6-one a.)

L-2-Benzyl-6-ethoxycarbonyl-2,6-diazabicyclo[3.3.0]-octane

Ethyl chloroformate (3.7 g, 33.8 mmoles) was added dropwise to a mixture of 5.7 g (28.2 mmoles) of L-2-benzyl-2,6-diazabicyclo[3.3.0]octane, 3.1 g (31.0 mmoles) of triethylamine in 0.5 liter of ether and was stirred overnight. The resulting solid material was filtered off and the filtrate was concentrated. The crude product (6.0 g, 81% of theory) was used in the following step without further purification.

Rf=0.7 (Merck, thin-layer chromatography prepared plates, silica gel 60 $F_{254}$; eluting agent: dichloromethane/methanol/concentrated ammonia 90/10/1, v/v/v).

b.) L-6-Methyl-2,6-diazabicyclo[3.3.0]octane

A mixture of 6.0 g (22.8 mmoles) of L-2-benzyl-6-ethoxycarbonyl-2,6-diazabicyclo[3.3.0]octane and 0.87 g (22.8 mmoles) of lithium aluminium hydride in 200 ml of ether was heated for 5 hours under reflux. 5 ml of 30% strength aqueous caustic soda were then added dropwise while cooling with ice and the solution was decanted off from the white precipitate. The ether solution was dried and concentrated, the remaining oily L-2-benzyl-6-methyl- 2,6-diazabicyclo[3.3.0]octane (4.8 g, 97% of theory) was uniform according to thin-layer chromatographic analysis [Rf =0.35 (Merck, thin-layer chromatography prepared plates, silica gel 60 $F_{254}$;

eluting agent: dichloromethane/methanol/concentrated ammonia 90/10/1, v/v/v)]and was hydrogenated for 5 hours at 60° C. in an autoclave with addition of 0.5 g of palladium on charcoal (10%) and in ethanol. The reaction mixture was concentrated under reduced pressure and used as the crude product (3.3 g) for further reactions.

c.)

L-5,11-Dihydro-11-[[6-methyl-2,6-diazabicyclo[3.3.0]-oct-2-yl]carbonyl]-6H-pyrido[2,3-b][1,4]benzodiazepin-6-one A mixture of 0.95 g (3.5 mmoles) of 11-(chlorocarbonyl)-5,11-dihydro-6H-pyrido[2,3-b][1,4]benzodiazepin-6-one and 0.40 g (3.2 mmoles) of L-2-methyl-2,6-diazabicyclo-[3.3.0]octane was stirred for 3 hours in 50 ml of acetonitrile, then concentrated under reduced pressure. The residue was divided between water and ethyl acetate, in which 0.4 g (3.5 mmoles) of maleic acid had previously been dissolved. The aqueous phase was extracted a further two times using ethyl acetate and rendered alkaline by adding 0.5 g of potassium carbonate. The aqueous phase was extractedexhaustively using dichloromethane and the combined organic extracts were dried and concentrated. The residue was purified using column chromatography (silica gel 63-200 μm; mobile phase: dichloromethane/methanol/concentrated ammonia 1200/50/5, v/v/v). 0.44 g (38% of theory) of crystals of m.p. 220°-222° C. (acetonitrile) were obtained.

EXAMPLE 7

L-5,11-Dihydro-8-methyl-11-[[6-methyl-2,6-diazabicyclo[3.3.0]oct-2-yl]carbonyl]-6H-pyrido[2,3-b][1,4]benzodiazepin-6-one Prepared analogously to Example 6c from 2.0 g (7.0 mmoles) of 11-(chlorocarbonyl)-5,11-dihydro-8-methyl-6H-pyrido-[2,3-b][1,4]benzodiazepin-6-one, 0.8 g (6.3 mmoles) of L-2-methyl-2,6- diazabicyclo[3.3.0]octane and 100 ml of acetonitrile in a yield of 25%. Colourless crystals of m.p. 160°-165° C.

EXAMPLE 8

L-6,11-Dihydro-11-[[6-methyl-2,6-diazabicyclo[3.3.-0]oct-2-yl]carbonyl]-5H-pyrido[2,3-b][1,5]benzodiazepin-5-one Prepared analogously to Example 6c from 1.9 g (7.0 mmoles) of 11-(chlorocarbonyl)-6,11-dihydro-5H-pyrido [2,3-b][1,5]benzodiazepin-5-one, 0.8 g (6.3 mmoles) of L-2-methyl-2,6- diazabicyclo[3.3.0]octane and 100 ml of acetonitrile in a yield of 54% of theory. $[\alpha]_D^{20} = +314°$.

EXAMPLE 9

D-5,11-Dihydro-11-[[6-methyl-2,6-diazabicyclo[3.3.-0]oct-2-yl]carbonyl]-6H-pyrido[2,3-b][1,4]benzodiazepin-6-one Prepared analogously to Example 6c from 0.95 g (3.5 mmoles) of 11-(chlorocarbonyl)-5,11-dihydro-6H-pyrido [2,3-b][1,4]benzodiazepin-6-one, 0.40 g (3.2 mmoles) of D-2-methyl-2,6- diazabicyclo[3.3.0]octane in 50 ml of acetonitrile. Colourless crystals of m.p. 160°-165° C. in a yield of 38% of theory.

EXAMPLE 10

D-5,11-Dihydro-8-ethyl-11-[[6-methyl-2,6-diazabicyclo-[3.3.0]oct-2-yl]carbonyl]-6H-pyrido[2,3-b][1,4]-benzodiazepin-6-one Prepared analogously to Example 6c from 1.6 g (5.3 mmoles) of 8- ethyl-11-(chlorocarbonyl)-5,11-dihydro-6H-pyrido [2,3- b][1,4]benzodiazepin-6-one, 0.67 g (5.3 mmoles) of D-2-methyl-2,6-diazabicyclo[3.3.0]octane in 67% yield. Colourless crystals of m.p. 162°-165° C.

EXAMPLE 11

D-6,11-Dihydro-11-[[6-methyl-2,6-diazabicyclo[3.3.-0]oct-2-yl]carbonyl]-5H-pyrido[2,3-b][1,5]benzodiazepin-5-one Prepared analogously to Example 6c from 0.95 g (3.5 mmoles) of 11-(chlorocarbonyl)-6,11-dihydro-5H-pyrido [2,3-b][1,5]benzodiazepin-5-one, 0.40 g (3.2 mmoles) of D-2-methyl-2,6-diazabicyclo[3.3.0]octane in a yield of 42 Colourless crystals of m.p. 172°-174° C., $[\alpha]_D^{20} = +284°$.

EXAMPLE 12

L-5,11-Dihydro-11-[[6-isopropyl-2,6-diazabicyclo[3.3.-0]oct-yl]carbonyl]-6H-pyrido[2,3-b][1,4]benzodiazepin-6-one a.) L-2-Isopropyl-2,6-diazabicyclo[3.3.0]octane A mixture of 10.0 g (34 mmoles) of L-2,6-dibenzyl-2,6-diazabicyclo[3.3.0]octane, 10.0 g of acetone (172 mmoles) and ethanol (1.0 liter) was hydrogenated for 20 hours at 60° C. with addition of 1 g of palladium on charcoal (10%). The catalyst was filtered off and the reaction mixture was concentrated. The residue was purified by means of column chromatography (silica gel 60-200 μm; mobile phase: dichloromethane/methanol/concentrated ammonia 100/10/1, v/v/v). 1.2 g (26% of theory) of L-2-isopropyl-2,6-diazabicyclo[3.3.0]octane and 1.5 g (45% of theory) of 2,6-diazabicyclo[3.3.0]octane were eluted.

L-2-Isopropyl-2,6-diazabicyclo[3.3.0]octane. Rf=0.2 (Merck, thin-layer chromatography prepared plates, silica gel 60 $F_{254}$; eluting agent: dichloromethane/methanol/concentrated ammonia 150/50/5, v/v/v).

b.)

L-5,11-Dihydro-11-[[6-isopropyl-2,6-diazabicyclo[3.3.-0]oct-2-yl]carbonyl]-6H-pyrido[2,3-b][1,4]benzodiazepin-6-one Prepared analogously to Example 6c from 2.1 g (7.8 mmoles) of 11-(chlorocarbonyl)-5,11-dihydro-6H-pyrido[2,3-b][1,4]benzodiazepin- 6-one and 1.2 g (7.8 mmoles) of L-2-isopropyl-2,6- diazabicyclo[3.3.0]octane in 50 ml of dry dimethylformamide in a yield of 56% of theory.

Rf=0.2 (Merck, thin-layer chromatography prepared plates, silica gel 60 $F_{254}$; eluting agent: dichloromethane/methanol/concentrated ammonia 140/10/1, v/v/v).

Calculated: C, 67.50; H, 6.44; N, 17.89. Found: C, 67.66; H, 6.65,N, 17.36.

EXAMPLE 13 cis-5,11-Dihydro-11-[[8-methyl-2,8-diazabicyclo[4.4.0]-dec-2-yl]carbonyl]-6H-pyrido[2,3-b][1,4]benzodiazepin-6-one and trans-5,11-dihydro-11-[[8-methyl-2,8-diazabicyclo[4.4.0]dec-2-yl]carbonyl]-6H-pyrido[2,3-b][1,4]benzodiazepin-6-one A mixture of 1.64 g (5.0 mmoles) of 11-(chlorocarbonyl)-5,11-dihydro-6H-pyrido[2,3-b][1,4]benzodiazepin-6-one, 0.8 g (5.2 mmoles) of 8-methyl-2,8-diazabicyclo[4.4.0]decane and 0.85 ml (6.0 mmoles) of triethylamine in 20 ml of tetrahydrofuran was stirred for 3 hours at ambient temperature. The reaction mixture was concentrated in vacuo and the residue was divided between ethyl acetate and dilute aqueous potassium carbonate solution. The organic phase was separated off, dried and concentrated in vacuo. Chromatographic purification took place on silica gel (30–60 μm) using the solvent mixture ethyl acetate/methanol/concentrated ammonia 70/30/1, v/v/v. The two main fractions were concentrated, ground with acetonitrile and the resulting precipitate was filtered off. 100 mg (5% of theory) of crystals of m.p. 230°–233° C., which were identified as trans compound using spectroscopic methods, were obtained from the main fraction eluted initially. The subsequent main fraction contained 200 mg (10% of theory) of the crystalline cis compound of m.p. 160°–161° C.

EXAMPLE 14

5,11-[[10-methyl-4,10-diazatricyclo[5.2.1.0$^{2,6}$]dec-4-yl]carbonyl]-6H-pyrido[2,3-b][1,4]benzodiazepin-6-one A mixture of 1.44 g. (5.25 mmoles) of 11-(chlorocarbonyl)-5,11-dihydro-6H-pyrido[2,3-b][1,4]benzodiazepin-6-one, 0.8 g (5.25 mmoles) of 10-methyl-4,10-diazatricyclo[5.2.1.0$^{2,6}$]decane and 0.73 ml (5.25 mmoles) of triethylamine was stirred in 80 ml of acetonitrile for 8 hours at ambient temperature. The suspension was filtered free from solids under suction and the filtrate obtained was concentrated. The residue was recrystallised from ethyl acetate, the crystals were taken up in methylene chloride and treated with aqueous sodium carbonate solution. The organic phase was then separated off and the aqueous phase was extracted a further two times using methylene chloride. The combined organic phases were dried over sodium sulphate, filtered and concentrated in vacuo. The residue was then purified over a silica gel column (silica gel 30–60 μm; mobile phase: cyclohexane/ethyl acetate/methanol/concentrated ammonia 2/2/10/1, v/v/v/v) and then recrystallised once again from ethyl acetate. 0.53 g (26% of theory) of white crystals of m.p. 218°–220° C. was obtained. $C_{22}H_{23}N_5O_2$ (389.46);

Calculated: C, 67.85. H; 5.95, N, 17.98. Found: C, 67.98; H, 6.10; N, 18.18.

EXAMPLE 15

5,10-Dihydro-5-[[10-methyl-4,10-diazatricyclo[5.2.1.0$^{2,6}$]dec-4-yl]carbonyl]-11H-dibenzo[b,e][1,4]diazepin-11-one Prepared analogously to Example 14 from 1.40 g (5.1 mmoles) of 5-(chlorocarbonyl)-5,10-dihydro-11H-dibenzo [b,e][1,4]diazepin-11-one, 0.78 g (5.12 mmoles) of 10-methyl-4,10- diazatricyclo[5.2.1.0z.$^{\circ}$ ]decane, 0.7 ml (5.1 mmoles) of triethylamine and 60 ml of acetonitrile in a yield of 30% of theory.

Colourless crystals of m.p. 230°–233° C.

$C_{22}H_{24}N_4O_2$ (388.47);

Calculated: C, 71.11; H, 6.23, N, 14.42. Found: C, 70.75; H, 6.34; N, 14.42.

EXAMPLE 16

L-4,9-Dihydro-3-methyl-4-[[6-methyl-2,6-diazabicyclo[3.3.0]oct-2-yl]carbonyl]-10H-thieno[3,4-b][1,5]benzodiazepin-10-one Prepared analogously to Example 6c from 4-(chlorocarbonyl)-4,9- dihydro-3-methyl-10H-thieno [3,4-b][1,5]benzodiazepin-10-one and L-2-methyl-2,6-diazabicyclo[3.3.0]octane in a yield of 37% of theory. Colourless crystals of m.p. 95°–100° C. (acetonitrile).

EXAMPLE 17

L-3-Chloro-1-methyl-4-[[6-methyl-2,6-diazabicyclo[3.3.0]oct-2-yl]carbonyl]-1,4,9,10-tetrahydropyrrolo[3,2-b][1,5]benzo diazepin-10-one Prepared analogously to Example 6c from 3-chloro-4-(chlorocarbonyl)-1-methyl-1,4,9,10-tetrahydropyrrolo [3,2-b][1,5]benzodiazepin-10-one and L-2-methyl-2,6-diazabicyclo[3.3.0]octane in a yield of 56% of theory. Colourless crystals of m.p. 200°–203° C.

EXAMPLE 18 trans-5,11-Dihydro-11-[[7-methyl-2,7-diazabicyclo[4.4.0]dec-2-yl]carbonyl-6H-pyrido[2,3-b][1,4]benzodiazepin-6-one a.) trans-2,7-Diazabicyclo[4.4.0]decane 1,5-Naphthyridine (5.0 g, 38.4 mmoles) in 450 ml of amyl alcohol was heated under reflux and sodium (21.3 g, 0.92 mole) was added in portions to the reaction mixture over a period of 30 minutes. 84 ml of concentrated hydrochloric acid were then added. The organic phase was separated off, washed twice using water and the combined aqueous extracts were extracted a further two times using ether. The ether phases were discarded, the aqueous phase was rendered basic using caustic soda while cooling with ice and the desired product was removed by repeated extraction using dichloromethane. The combined dichloromethane phases were dried and concentrated under reduced pressure. Quantitative yield (5.8 q) of crystals of m.p. 174°–176° C. (ethyl acetate).

b.) trans-2-Methyl-2,7-diazabicyclo[4.4.0]decane

A mixture of trans-2,7-diazabicyclo[4.4.0]decane (1.4 g, 10 mmoles), 37% aqueous formaldehyde solution (0.6 ml, 8 mmoles) and 0.5 g of palladium on charcoal (10%) was hydrogenated for 10 hours at 60° C. under a pressure of 3 to 4 bar. Hydrogenation under the conditions given above was continued after adding a further 0.3 ml of the 37% aqueous formaldehyde solution, the reaction mixture was then concentrated and digested with petrolether. The petrolether solution was concentrated under reduced pressure and the oily residue (1.2 g) was used for further reactions without further purification.

c.)trans-5,11-Dihydro-11-[[7-methyl-2,7-diazabicyclo[4.4.0]dec-2-yl]carbonyl-6H-pyrido[2,3-b][1,4]benzodiazepin-6-one A mixture of 0.84 g (3.1 mmoles) of 11-(chlorocarbonyl)-5,11-dihydro-6H-pyrido[2,3-b][1,4]benzodiazepin-6-one and 0.43 g (2.8 mmoles) of trans-2-methyl-2,7- diazabicyclo[4.4.0]decane was stirred in 80 ml of acetonitrile for 24 hours and then concentrated under reduced pressure. The residue was divided between water and ethyl acetate, in which 0.3 g of maleic acid had been previously dissolved. The aqueous phase was extracted once again using ethyl acetate, rendered alkaline by adding potassium carbonate and then extracted exhaustively using dichloromethane. The combined organic extracts were dried, concentrated and purified by means of column chromatography (silica gel 63–200 μm, mobile phase:

dichloromethane/methanol/concentrated ammonia 90/10/1, v/v/v). 0.2 g of the title compound (18% of theory) was obtained.

EXAMPLE 19 trans-6,11-Dihydro-11-[[6-methyl-2,6-diazabicyclo[4.4.0]dec-2-yl]carbonyl]-5H-pyrido[2,3-b][1,5]benzodiazepin-5-one Prepared analogously to Example 18c from 0.84 g (3.1 mmoles) of 11-(chlorocarbonyl)-6,11-dihydro-5H-pyrido [2,3-b][1,5]benzodiazepin-5-one, 0.43 g (2.8 mmoles) of trans-2-methyl-2,7-diazabicyclo[4.4.0]decane in a yield of 37%.

EXAMPLE 20

L-5,11-Dihydro-11-[[6-methyl-2,6-diazabicyclo[3.3.0]oct-2-yl]carbonyl]-6H-pyrido[2,3-b][1,4]benzodiazepin-6-one 2.6 g (0.021 mole) of L-2-methyl-2,6-diazabicyclo [3.3.0]octane were added dropwise to a mixture consisting of 11.2 ml of a 20% strength solution of phosgene in toluene, 50 ml of acetonitrile and 2.4 g (0.023 mole) of anhydrous sodium carbonate while externally cooling with ice. After 60 minutes, 4.5 g (0.021 mole) of 5,11-dihydro-6H-pyrido[2,3-b][1,4]benzodiazepin-6-one were added and the mixture was heated under reflux for 4 hours. The hot mixture was filtered, the precipitate was washed three times using 10 ml of hot acetonitrile each time and the combined filtrates were concentrated in vacuo to a total volume of 15 ml. The solution was cooled in an ice bath and the resulting crystal paste was filtered under suction. Recrystallisation from acetonitrile produced 2.1 g (27% of theory) of colourless crystals of m.p. 220°–222° C., identical to the preparation made as in Example 6c according to mixed melting point and spectroscopic data.

5,11-Dihydro-11-[[7-methyl-3,7-diazabicyclo[3.3.0]oct-3-yl]carbonyl]-6H-pyrido[2,3-b][1,4]benzodiazepin-6-one of m.p. 157°–159° C. (acetonitrile)

5,11-dihydro-11-[[10-methyl-4,10-diazatricyclo[5.2.1.0$^{2,6}$]dec-4-yl]carbonyl]-6H-pyrido[2,3-b][1,4]benzodiazepin-6-one of m.p. 218°–220° C. (ethyl acetate) were obtained in corresponding manner.

The preparation of pharmaceutical formulations is described below using some examples:

EXAMPLE I

Tablets having 5 mg of
D-6,11-dihydro-11-[[6-methyl-2,6-diazabicyclo[3.3.0]oct-2-yl]carbonyl]-5H-pyrido
[2,3-b][1,5]benzodiazepin-5-one

| Composition: 1 tablet contains: | |
|---|---|
| Active ingredient | 5.0 mg |
| Lactose | 148.0 mg |
| Potato starch | 65.0 mg |
| Magnesium stearate | 2.0 mg |
| | 220.0 mg |

Preparation process

A 10% strength mucilage is prepared from potato starch by heating. The active substance, lactose and the remaining potato starch are mixed and granulated with the above mucilage through a sieve of mesh width 1.5 mm. The granules are dried at 45° C., rubbed once again through the above sieve, mixed with magnesium stearate and pressed to give tablets.
Tablet weight: 220 mg
Stamp: 9 mm

EXAMPLE II

Coated tablets having 5 mg of
D-6,11-dihydro-11-[[6-methyl-2,6-diazabicyclo[3.3.0]oct-2-yl]carbonyl]-5H-pyrido[2,3-b][1,5]benzodiazepin-5-one The tablets prepared according to Example I are coated with a shell consisting essentially of sugar and talc in accordance with known processes. The finished coated tablets are polished with the aid of beeswax.
Coated tablet weight: 300 mg

EXAMPLE III

Ampoules having 10 mg of D-6,11-dihydro-11-[[6-methyl-2,6-diazabicyclo[3.3.0]oct-2-yl]carbonyl]-5H-pyrido[2,3-b]1,5]benzodiazepin-5-one

| Composition: 1 ampoule contains: | |
|---|---|
| Active ingredient | 10.0 mg |
| Sodium chloride | 8.0 mg |
| Distilled water ad | 1 ml |

Preparation process

The active substance and sodium chloride are dissolved in distilled water and the solution is then made up to the given volume. The solution is sterile filtered and poured into 1 ml ampoules.
Sterilisation: 20 minutes at 120° C.

EXAMPLE IV

Suppositories having 20 mg of
D-6,11-dihydro-11-[[6-methyl-2,6-diazabicyclo[3.3.0]oct-2-yl]carbonyl]-5H-pyrido[2,3-b][1,5]benzodiazepin-5-one

| Composition: 1 suppository contains: | |
|---|---|
| Active ingredient | 20.0 mg |
| Suppository substance (for example Witepsol W 45 ®) | 1,680.0 mg |
| | 1.700.0 mg |

Preparation process

The finely powdered active substance is suspended in the molten suppository substance cooled to 40° C. The substance is poured at 37° C. into slightly pre-cooled suppository moulds.

Suppository weight 1.7 g

EXAMPLE V

Drops containing D-6,11-dihydro-11-[[6-methyl-2,6-diazabicyclo[3.3.0]oct-2-yl]carbonyl]-5H-pyrido[2,3-b][1,5]benzodiazepin-5-one

| Composition: 100 ml of drops solution contain: | |
|---|---|
| Methyl p-hydroxybenzoate | 0.035 g |
| Propyl p-hydroxybenzoate | 0.015 g |
| Aniseed oil | 0.05 g |
| Menthol | 0.06 g |
| Pure ethanol | 10.0 g |
| Active ingredient | 0.5 g |
| Sodium cyclamate | 1.0 g |
| Glycerol | 15.0 g |
| Distilled water ad | 100.0 ml |

Preparation process

The active substance and sodium cyclamate are dissolved in approximately 70 ml of water and glycerol is added. p-Hydroxybenzoate, aniseed oil and menthol are dissolved in ethanol and this solution is added to the aqueous solution with stirring. The solution is then made up to 100 ml with water and filtered free of floating particles.

What is claimed is:

1. A compound of formula I

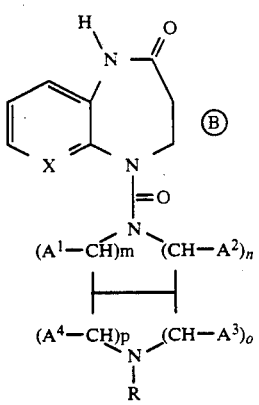

in which

]$\textcircled{B}$ represents one of the divalent groups

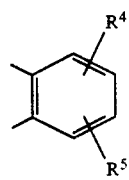

(S)

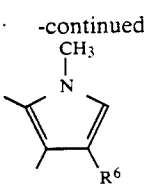

(T)

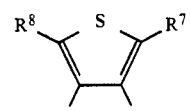

(U)

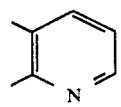

(V)

and

X, R, $R^4$, $R^5$, $R^6$, $R^7$, $R^8$, m, n, o, p, $A^1$, $A^2$, $A^3$ and $A^4$ have the following meanings:

X is a =CH—group or a nitrogen atom,

R is a straight-chain or branched alkyl radical having 1 to 4 carbon atoms, which may optionally also be substituted by a phenyl monosubstituted or disubstituted by chlorine, bromine, fluorine, methyl or methoxy, $R^4$ and $R^5$, which may be the same or different from one another, denote a hydrogen, fluorine, chlorine or bromine atom or an alkyl group having 1 to 4 carbon atoms, $R^6$ is a hydrogen or chlorine atom or a methyl group, $R^7$ and $R^8$, which may be the same or different from one another, denote hydrogen atoms or alkyl groups having 1 to 4 carbon atoms, however, $R^8$ may also additionally denote a halogen atom, m, n, o and p each denote the numbers 0, 1, 2 or 3 with the following limitations:

the sum of m+n and the sum of o+p each denote the numbers 1, 2 or 3, the sum of n+o and the sum of m+p each denote the numbers 1, 2, 3, 4 or 5, wherein, however, the sum of m+n+o+p must always be greater than 2, $A^1$, $A^2$, $A^3$ and $A^4$ denote hydrogen atoms; for the case where m, n, o and p each denote the number 1, either $A^1$ and $A^2$ together or $A^3$ and $A^4$ together may also represent an ethylene bridge, an isomer thereof or a physiologically acceptable salt thereof with an inorganic or organic acid.

2. The compound as recited in claim 1 wherein

X denotes a nitrogen atom and ]$\textcircled{B}$ denotes the group (S) or

X denotes a =CH—group and ]$\textcircled{B}$ denotes the group (V),

R represents the methyl group, $R^4$ and $R^5$, which may be the same or different from one another, each represent a hydrogen, fluorine or chlorine atom, the methyl or ethyl group, and m=0, n=2, o=0, p=2 or m, n, o and p are each equal to 1, an isomer thereof or a physiologically acceptable salt thereof with an inorganic or organic acid.

3. The compound as recited in claim 1, L-5,11-dihydro-11-[[6-methyl-2,6-diazabicyclo[3.3.0]oct-2-yl]carbonyl]-6H-pyrido[2,3-b][1,4]benzodiazepin-6-one, an isomer thereof, or a physiologically acceptable salt thereof with an inorganic or organic acid.

4. The compound as recited in claim 1, D-6,11-dihydro-11-[[6-methyl-2,6-diazabicyclo[3.3.0]oct-2-yl]carbonyl]-5H-pyrido[2,3-b][1,5]benzodiazepin-5-one, an isomer thereof, or a physiologically acceptable salt thereof with an inorganic or organic acid.

5. The compound as recited in claim 1, 5,11-dihydro-11-[[7-methyl-3,7-diazabicyclo[3.3.0]oct-3-yl]carbonyl]-6H-pyrido[2,3-b][1,4]benzodiazepin-6-one, an isomer thereof, or a physiologically acceptable salt thereof with an inorganic or organic acid.

6. A pharmaceutical composition of matter comprising a therapeutically effective amount of a compound as recited in claim 1 and a pharmaceutically acceptable carrier.

7. A method of treating cholinergically induced spasms and motility disturbances in the gastrointestinal tract and in the region of the evacuating bile ducts in a warm-blooded animal which comprises administering to said animal a therapeutically effective amount of a compound as recited in claim 1.

8. A method of treating cystits and of spasms from urelithiasis in a warm-blooded animal which comprises administering to said animal a therapeutically effective amount of a compound as recited in claim 1.

9. A method of treating incontinence in a warm-blooded animal which comprises administering to said animal a therapeutically effective amount of a compound as recited in claim 1.

10. A method of treating bronchial asthma and bronchitis in a warm-blooded animal which comprises administering to said animal a therapeutically effective amount of a compound as recited in claim 1.

11. A method of treating ischaemic heart disease in a warm-blooded animal which comprises administering to said animal a therapeutically effective amount of a compound as recited in claim 1.

* * * * *